United States Patent
Li et al.

(10) Patent No.: US 12,171,850 B2
(45) Date of Patent: Dec. 24, 2024

(54) PERSONAL CARE COMPOSITIONS

(71) Applicant: Colgate-Palmolive Company, New York, NY (US)

(72) Inventors: Min Li, Bridgewater, NJ (US); Aixing Fan, Bridgewater, NJ (US); Thomas Boyd, Metuchen, NJ (US); Nadia Soliman, East Brunswick, NJ (US); Vinay Bhardwaj, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 138 days.

(21) Appl. No.: 17/310,990

(22) PCT Filed: Mar. 9, 2020

(86) PCT No.: PCT/US2020/021657
§ 371 (c)(1),
(2) Date: Sep. 3, 2021

(87) PCT Pub. No.: WO2020/185654
PCT Pub. Date: Sep. 17, 2020

(65) Prior Publication Data
US 2022/0079854 A1    Mar. 17, 2022

Related U.S. Application Data

(60) Provisional application No. 62/815,494, filed on Mar. 8, 2019.

(51) Int. Cl.
*A61K 8/365* (2006.01)
*A61K 8/34* (2006.01)
*A61K 8/36* (2006.01)
*A61Q 15/00* (2006.01)
*A61Q 17/00* (2006.01)
(Continued)

(52) U.S. Cl.
CPC .............. *A61K 8/365* (2013.01); *A61K 8/345* (2013.01); *A61K 8/36* (2013.01); *A61Q 15/00* (2013.01); *A61Q 17/005* (2013.01); *A61Q 19/007* (2013.01); *A61Q 19/10* (2013.01)

(58) Field of Classification Search
None
See application file for complete search history.

(56) References Cited

U.S. PATENT DOCUMENTS 2,350,047 A    5/1944   Emil et al.
5,262,153 A   11/1993   Mishima et al.
(Continued)

FOREIGN PATENT DOCUMENTS

CN    101107045         1/2008
CN    101182299 A   *   5/2008  ........... A61K 31/137
(Continued)

OTHER PUBLICATIONS

MedicalNewsToday (on-line website: [(https://www.medicalnewstoday.com/articles/324784, Jul. 2022, pp. 1-14)] (Year: 2022).*
(Continued)

*Primary Examiner* — Kyung S Chang

(57) ABSTRACT

Described herein are personal care compositions comprising a complex comprising a plurality of short chain fatty acids; along with methods of making and using same.

7 Claims, 4 Drawing Sheets

(51) Int. Cl.
*A61Q 19/00* (2006.01)
*A61Q 19/10* (2006.01)

(56) References Cited

U.S. PATENT DOCUMENTS

| | | | |
|---|---|---|---|
| 5,618,522 | A | 4/1997 | Deckner et al. |
| 5,785,962 | A | 7/1998 | Hinz et al. |
| 6,017,548 | A | 1/2000 | Epstein et al. |
| 6,139,850 | A | 10/2000 | Hahn et al. |
| 6,365,137 | B1 | 4/2002 | Aust et al. |
| 7,250,174 | B2 | 7/2007 | Lee et al. |
| 8,227,426 | B2 | 7/2012 | Gupta et al. |
| 8,435,955 | B2 | 5/2013 | Masui et al. |
| 8,673,327 | B2 | 3/2014 | Lemoine et al. |
| 8,741,357 | B2 | 6/2014 | Lamy et al. |
| 8,802,065 | B2 | 8/2014 | Oshimura et al. |
| 8,933,131 | B2 | 1/2015 | Carter et al. |
| 8,992,898 | B2 | 3/2015 | Klingman |
| 9,566,223 | B2 | 2/2017 | Klingman |
| 9,668,948 | B2 | 6/2017 | Klingman |
| 9,713,604 | B2 | 7/2017 | Dreher |
| 10,071,103 | B2 | 9/2018 | Sengupta et al. |
| 10,406,085 | B2 | 9/2019 | Dubovoy et al. |
| 10,532,014 | B2 | 1/2020 | Lesniak et al. |
| 10,561,593 | B2 | 2/2020 | Wu |
| 10,638,755 | B2 | 5/2020 | Pesaro et al. |
| 10,864,147 | B2 | 12/2020 | Hilliard, Jr. et al. |
| 10,933,000 | B2 | 3/2021 | Hilliard, Jr. et al. |
| 11,090,249 | B2 | 8/2021 | Mitchell et al. |
| 11,104,868 | B2 | 8/2021 | Hardy et al. |
| 2003/0053970 | A1 | 3/2003 | Bruening et al. |
| 2004/0076654 | A1 | 4/2004 | Vinson et al. |
| 2006/0182708 | A1 | 8/2006 | Bockmuhl et al. |
| 2007/0167529 | A1 | 7/2007 | Walton et al. |
| 2007/0243155 | A1 | 10/2007 | Bottiglieri et al. |
| 2008/0187562 | A1 | 8/2008 | Fan et al. |
| 2008/0206170 | A1 | 8/2008 | Nivaggioli et al. |
| 2008/0299068 | A1 | 12/2008 | Omura et al. |
| 2010/0189753 | A1 | 7/2010 | Van Bavel et al. |
| 2012/0006348 | A1 | 1/2012 | Grollier et al. |
| 2013/0059929 | A1 | 3/2013 | Koehler et al. |
| 2014/0205555 | A1 | 7/2014 | Gale et al. |
| 2015/0050227 | A1 | 2/2015 | Liu et al. |
| 2015/0202136 | A1* | 7/2015 | Lanzalaco ............ A61K 8/604 514/61 |
| 2016/0151257 | A1 | 6/2016 | Klingman |
| 2017/0183452 | A1 | 6/2017 | Panandiker et al. |
| 2018/0177692 | A1 | 6/2018 | Garcia et al. |
| 2019/0183780 | A1 | 6/2019 | Pan et al. |
| 2019/0270951 | A1 | 9/2019 | Hardy et al. |
| 2020/0016053 | A1 | 1/2020 | Hilliard, Jr. et al. |
| 2020/0405674 | A1 | 12/2020 | Schiller et al. |
| 2021/0275418 | A1 | 9/2021 | Bhardwaj |
| 2021/0275419 | A1 | 9/2021 | Li |
| 2021/0283025 | A1 | 9/2021 | Das et al. |
| 2021/0299020 | A1 | 9/2021 | Cruz et al. |
| 2022/0031591 | A1 | 2/2022 | Botto et al. |
| 2022/0079854 | A1 | 3/2022 | Li et al. |
| 2022/0395437 | A1 | 12/2022 | Leva |

FOREIGN PATENT DOCUMENTS

| | | | |
|---|---|---|---|
| CN | 101192299 A | * | 6/2008 |
| CN | 101820753 | | 9/2010 |
| CN | 103690380 | | 4/2014 |
| CN | 109259188 | | 1/2019 |
| DE | 19643585 | | 4/1998 |
| DE | 102004032734 | | 10/2005 |
| EP | 0345082 | | 12/1989 |
| EP | 0749749 | | 12/1996 |
| EP | 1443892 | | 8/2004 |
| EP | 1510200 | | 3/2005 |
| EP | 1526827 | | 5/2005 |
| EP | 2353579 | | 8/2011 |
| EP | 2374835 | | 10/2011 |
| JP | H09110650 | | 4/1997 |
| JP | 2004-089177 | | 3/2004 |
| KR | 20120070104 | | 6/2012 |
| KR | 101189187 | | 10/2012 |
| KR | 20140039548 | | 4/2014 |
| KR | 20150011060 | | 1/2015 |
| KR | 101503979 | | 3/2015 |
| KR | 101768921 | | 8/2017 |
| WO | 2009/020582 | | 2/2009 |
| WO | 2009/046008 | | 4/2009 |
| WO | 2010/044076 | | 4/2010 |
| WO | 2011/099849 | | 8/2011 |
| WO | 2017/030560 | | 2/2017 |
| WO | 2018/022016 | | 2/2018 |
| WO | 2019/117858 | | 6/2019 |
| WO | 2020/052916 | | 3/2020 |
| WO | 2020/057761 | | 3/2020 |
| WO | 2020/185654 | | 9/2020 |
| WO | 2021/096518 | | 5/2021 |
| WO | 2021/183462 | | 9/2021 |
| WO | 2021/183464 | | 9/2021 |
| WO | 2022/063857 | | 3/2022 |
| WO | 2023/034493 | | 3/2023 |

OTHER PUBLICATIONS

CN10118229A—Google English Translation (Year: 2007).*
Du Couto et al., "antifungal activity of the piroctone olamine in intra-abdominal candidiasis", SpringerPlus (2016)5:468. (Year: 2016).*
Patel et al. "Postinflammatory hyperpigmentation: Review of pathogenesis, prevention, and treatment", Pigment International, Jul.-Dec. 2014, vol. 1, issue 2, pp. 59-69 (Year: 2014).*
Cork, "The role of *Staphylococcus aureus* in atopic eczema: treatment strategies", Journal of the European Academy of Dermatology and Venereology, vol. 7, Supplement 1, Jul. 1996, pp. 531-537. (Year: 1996).*
Colgate-Palmolive, 2021, "Atopicare Shower Cream", Mintel Database GNPD AN: 8747223.
International Search Report and the Written Opinion of the International Searching Authority issued in International Application PCT/US2022/042327 mailed Dec. 20, 2022.
Allies Group, 2017, "Promise Keeper Blemish Facial", Mintel Database GNPD AN: 5196555.
Briseis, 2005, "Intensity Classic Deo Roll-On", Mintel Database GNPD AN: 371579.
Coop, 2014, "Intimate Wash", Mintel Database GNPD AN: 2677521.
Dr. Dennis Gross Skincare, 2014, "Clinical Concentrate Radiance Booster", Mintel Database GNPD AN: 2350479.
Glamglow, 2012, "Super-Mud Clearing Treatment", Mintel Database GNPD AN: 1921209.
Glamglow, 2019, "Superserum 6-Acid Refining Treatment", Mintel Database GNPD AN: 6521601.
Glamglow, 2019, "Supertoner Exfoliating Acid Soution", Mintel Database GNPD AN: 6457009.
Institut Esthederm, 2011, "E.V.E. Essential Vital Elements Serum Source", Mintel Database GNPD AN: 1666406.
International Search Report and the Written Opinion of the International Searching Authority issued in International Application PCT/US2020/021657 mailed May 27, 2020.
International Search Report and the Written Opinion of the International Searching Authority issued in International Application PCT/US2021/021426 mailed Jun. 28, 2021.
International Search Report and the Written Opinion of the International Searching Authority issued in International Application PCT/US2021/021428 mailed Jun. 28, 2021.
Johnson & Johnson, 2006, "Micro Exfoliating Oxygenating Gel", Mintel Database GNPD AN: 598917.
Novartis Consumer Health, 2011, "Milk Body Lotion", Mintel Database GNPD AN: 1632704.
Personal Collection, 2018, "Shaveless Hair Minimizing Anti-Perspirant Deodorant Roll-On", Mintel Database GNPD AN: 5574907.
Skin Design London, 2017, "Acne On The Spot Serum", Mintel Database GNPD AN: 4688909.
WPI Thomson Database AN: 2019-11530B and CN 109259188.

(56) References Cited

OTHER PUBLICATIONS

Anonymous, "Ingredients of Filorga Ultimate Revitalizing Night Cream," retrieved from https://www.cosdna.com/chs/cosmetic_4251189624.html, published on May 16, 2015.

Anonymous, 2011, "E.V.E. Essential Vital Elements Serum Source", Mintel Database GNPD AN: 1666406.

Boyd (https://www.chemservice.com/news/2014/08/which-chemicals-make-deodorants-and-antiperspirants-work/), Aug. 22, 2014, pp. 1-2 (Year:2014).

International Search Report and the Written Opinion of the International Searching Authority issued in International Application PCT/US2019/061522 mailed May 12, 2020.

Evans et al., 2012, "Axillary skin biology and care", International Journal of Cosmetic Science, 34:389-395.

IFSCC, 1998, Antiperspirants-and-Deodorants: Principles of Underarm Technology, Micelle press IFSCC No. 6, pp. 1-61.

International Search Report and the Written Opinion of the International Searching Authority issued in International Application PCT/US2022/042563 mailed Jan. 20, 2023.

Laboratoire SVR, 2017, "48H Anti-Perspirant Deodorant Roll-on", Mintel Database GNPD AN: 5111953.

Cosinter, 2011, "Intimate Liquid Soap", Mintel Database GNPD AN: 1547745.

IFSCC Monograph, No. 6, "Antiperspirants-and-Deodorants: Principles of Underarm Technology," Micelle Press, 76 pages, 1998.

International Search Report and the Written Opinion of the International Searching Authority issued in International Application PCT/US2023/031519 mailed Nov. 30, 2023.

International Search Report and the Written Opinion of the International Searching Authority issued in International Application PCT/US2023/031632 mailed Nov. 30, 2023.

Pharma Solutions, 2022, "Cleansing Bar", Mintel Database GNPD AN: 9713532.

Celltrion Skincure, 2021, "Cleansing Oil & Blackhead", Mintel Database GNPD AN: 8549187.

Coreana Cosmetics, 2020, "Peeling Pad", Mintel Database GNPD AN: 7440987.

International Search Report and the Written Opinion of the International Searching Authority issued in International Application PCT/US2023/084725 mailed Mar. 28, 2024.

\* cited by examiner

PERSONAL CARE COMPOSITIONS

CROSS-REFERENCE TO RELATED APPLICATION

This application claims the benefit of priority from U.S. Provisional Application No. 62/815,494, filed Mar. 8, 2019, the contents of which are hereby incorporated herein in their entirety.

BACKGROUND

Probiotics are well known to have beneficial effects on skin health. Much effort has been put forth to improve the skin microflora balance. In particular, it is desirable to inhibit harmful bacteria, while promoting the growth of beneficial bacteria. However, the ability to provide this dual benefit still remains a challenge.

In addition, skin tends to lose its elasticity and/or firmness as it ages. Current options for maintaining skin elasticity and firmness are sub-optimal.

As such, embodiments of the present invention are designed to provide these, and other, benefits.

BRIEF SUMMARY

In some embodiments, the present invention provides personal care compositions comprising: a complex comprising a plurality of short chain fatty acids; and a cosmetically acceptable carrier.

In other embodiments, the present invention provides personal care compositions comprising a first component comprising a first short chain fatty acid; a second component comprising a second short chain fatty acid; and a third component comprising a third short chain fatty acid.

Still further embodiments of the present invention provide a biomimetic blend comprising: from about 8 to about 14 parts, by weight, lactic acid; from about 4 to about 6 parts, by weight, acetic acid; and from about 2 to about 3 parts, by weight, pyruvic acid.

While other embodiments provide methods of treating a body surface of a mammal (e.g. skin) in need thereof, the method comprising administering to the body surface of the patient, an effective amount of a personal care composition described herein or a biomimetic blend described herein.

DETAILED DESCRIPTION

Figure 1:
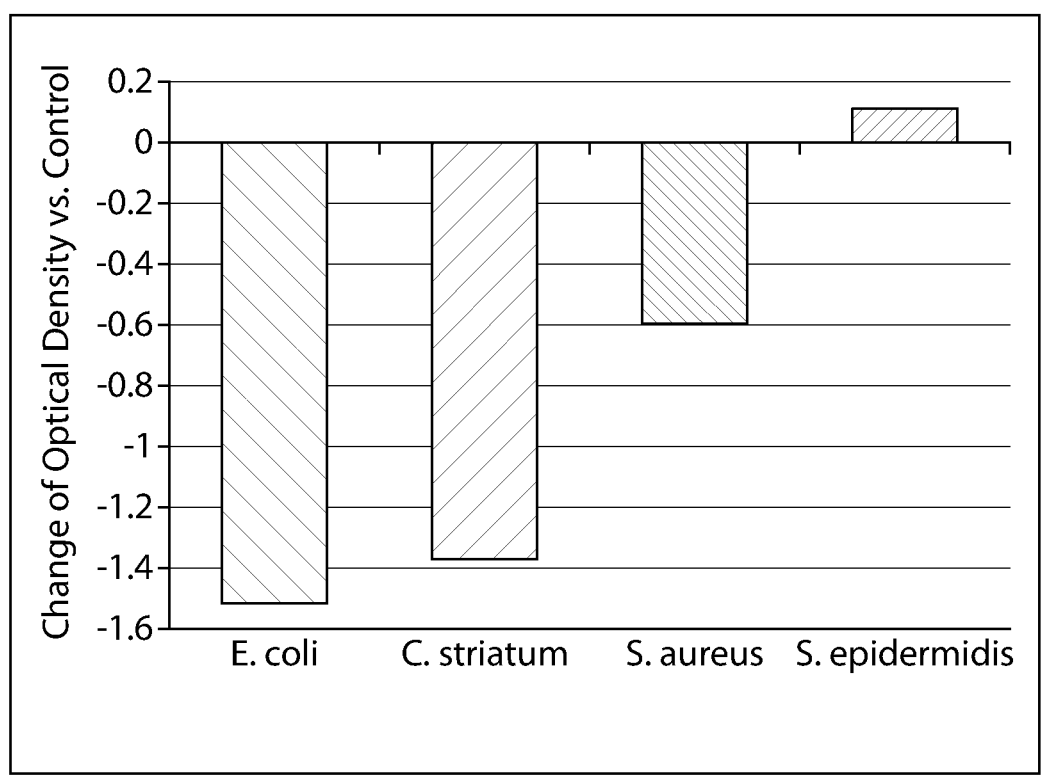
FIG. 1 depicts the impact that an exemplary composition of the present invention had on the growth of various bacteria.

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation.

As used herein and in the appended claims, the singular forms "a", "an", and "the" include plural references unless the context dictates otherwise. The singular form of any class of the ingredients refers not only to one chemical species within that class, but also to a mixture of those chemical species. The terms "a" (or "an"), "one or more" and "at least one" may be used interchangeably herein. The terms "comprising", "including", and "having" may be used interchangeably. The term "include" should be interpreted as "include, but are not limited to". The term "including" should be interpreted as "including, but are not limited to".

As used throughout, ranges are used as shorthand for describing each and every value that is within the range. Any value within the range can be selected as the terminus of the range.

The term "about" when referring to a number means any number within a range of 10% of the number. For example, the phrase "about 2.0 wt %" refers to a number between and including 1.800 wt % and 2.200 wt %.

All references cited herein are hereby incorporated by reference in their entireties. In the event of a conflict in a definition in the present disclosure and that of a cited reference, the present disclosure controls.

The abbreviations and symbols as used herein, unless indicated otherwise, take their ordinary meaning. The abbreviation "wt %" means percent by weight with respect to the personal care composition. The symbol "0" refers to a degree, such as a temperature degree or a degree of an angle. The symbols "h", "min", "mL", "nm", "µm" means hour, minute, milliliter, nanometer, and micrometer, respectively. The abbreviation "UV-VIS" as referring to a spectrometer or spectroscopy, means Ultraviolet-Visible. The abbreviation "rpm" means revolutions per minute.

The phrase "MRS agar" refers to De Man, Rogosa and Sharpe agar, which is a selective culture medium designed to favor the growth of *Lactobacillus*. The phrase "TSB medium" refers to tryptic soy broth or trypticase soy broth, which is used in microbiology laboratories as a culture broth to grow aerobic bacteria. The phrase "PBS wash" refers to phosphate-buffered saline wash. The abbreviation "qPCR" is quantitative polymerase chain reaction.

When referring to chemical structures, and names, the symbols "C", "H", and "O" mean carbon, hydrogen, and oxygen, respectively. The symbols "—", "=" and "≡" mean single bond, double bond, and triple bond respectively.

Any member in a list of species that are used to exemplify or define a genus, may be mutually different from, or overlapping with, or a subset of, or equivalent to, or nearly the same as, or identical to, any other member of the list of species. Further, unless explicitly stated, such as when reciting a Markush group, the list of species that define or exemplify the genus is open, and it is given that other species may exist that define or exemplify the genus just as well as, or better than, any other species listed.

For readability purposes, the chemical functional groups are in their adjective form; for each of the adjective, the word "group" is assumed. For example, the adjective "alkyl" without a nouns thereafter, should be read as "an alkyl group".

A systematic search for a probiotic composition that has beneficial effects on a person s skin has been undertaken. The search has yielded a unique probiotics complex which is the fermentation product of *Lactobacillus rhamnosus* with 2.5% xylitol. In vitro testing has shown that this technology balanced skin microflora by selectively inhibiting the growth of undesirable skin bacteria and maintaining/promoting the growth of desirable bacteria. However, the composition of the biological complex is highly complicated and largely unknown raising potential safety and regulatory concerns.

To deal with these unknowns, the chemical composition of the fermentation product has been analyzed, and a blend of several compounds that are present in the fermentation product have been prepared. This blend of several compounds mimics the fermentation product, and is thus referred to herein as "biomimetic blend".

The fermentation product showed the presence of three short-chain acids and glycerol. The three major short chain acids were identified and quantified using HPLC to be lactic acid, acetic acid and pyruvic acid.

A biomimetic blend was made by the three acids as the ratio of 4:2:1. In vitro testing showed that the biomimetic blend selectively inhibited the growth of undesirable skin bacteria, such as *Escherichia coli, Staphylococcus aureus*, odor causing bacteria, e.g. *Corynebacterium striatum* and promote the growth of desirable bacteria, e.g. *Staphylococuss epidermidi*.

*Escherichia coli* is a Gram-negative, facultative anaerobic, rod-shaped, coliform bacterium of the genus *Escherichia* that is commonly found in the lower intestine of warm-blooded organisms (endotherms). Most *E. coli* strains are harmless, but some serotypes can cause serious food poisoning in their hosts, and are occasionally responsible for product recalls due to food contamination.

*Staphylococcus aureus* is a Gram-positive, round-shaped bacterium that is a member of the Firmicutes, and it is a usual member of the microbiota of the body, frequently found in the upper respiratory tract and on the skin. It is often positive for catalase and nitrate reduction and is a facultative anaerobe that can grow without the need for oxygen. Skin infections are the most common form of *S. aureus* infection. This can manifest in various ways, including small benign boils, folliculitis, impetigo, cellulitis, and more severe, invasive soft-tissue infections.

*S. aureus* is extremely prevalent in persons with atopic dermatitis, more commonly known as eczema. It is mostly found in fertile, active places, including the armpits, hair, and scalp. Large pimples that appear in those areas may exacerbate the infection if lacerated. This can lead to staphylococcal scalded skin syndrome, a severe form of which can be seen in newborns.

*Staphylococcus epidermidis*, a Gram-positive bacterium, is a part of the normal human flora, typically the skin flora, and less commonly the mucosal flora. It is a facultative anaerobic bacteria.

Further tests of adding 0.6% blend into a commercially available body wash and application thereof to a skin tissue, showed the body wash to upregulate hydration related gene and tight junction gene and downregulated inflammation related gene expressions. This revolutionary technology is suitable to body wash, lotion or underarm product to provide skin microbiome benefits.

The present invention is directed to a personal care composition comprising a biomimetic blend comprising lactic acid, acetic acid and pyruvic acid at about 4:2:1 ratio; and a surfactant. In other embodiments, the present invention provides a complex comprising a salt of lactic acid; a salt of acetic acid; and a salt of pyruvic acid (e.g. sodium pyruvate).

One of the advantages of the present invention is that the personal care composition provides for an improved skin microflora balance.

Another advantage is that the application of the personal care composition inhibits the growth of harmful bacteria such as *Escherichia coli, Corynebacterium striatum*, and *Staphylococcus aureus*.

Still another advantage of the present invention is that the personal care composition promotes the growth of beneficial bacteria, such as *Staphylococcus epidermidis*.

A further advantage of personal care composition of the present invention is the use of the composition upregulated AQP, FASN, OCLN gene expression.

Additional advantage of personal care composition of the present invention is the use of the composition downregulated IL8 gene expression.

In some embodiments, the personal care compositions of the present invention improve skin barrier function and hydration. Without being bound by theory, the present inventors believe that the effects observed with the compositions described herein are the result of increasing filaggrin and Occludin expression.

In some embodiments, the present invention is directed to a personal care composition comprising a biomimetic blend and a cosmetically acceptable carrier. In some embodiments, the cosmetically acceptable carrier comprises a surfactant. In some embodiments, the personal care composition further comprises an ingredient known to have antiperspirant or deodorant effect. A personal care composition is any composition that is applied to a person, either neat, or as a mixture.

Personal care compositions include hair care, skin care, sun care, nail care, and oral care compositions. In some embodiments, the personal care composition is applied to the person's skin or scalp. Examples of personal care compositions include an antiperspirant, a deodorant, a body wash, a shower gel, a lotion, a bar soap, a soft soap, a shampoo, a hair conditioner, a sunscreen, and a cosmetic. The personal care composition may be classified and regulated by national or international regulatory agencies as a cosmetic, or as a drug.

A deodorant is a composition that is applied to the body of a person to prevent body odor caused by the bacterial breakdown of perspiration. A deodorant may be applied to any part of the body. Under selected embodiments, the deodorant is applicable to armpits and feet.

An antiperspirant is a composition that mitigates body odor as well as prevents sweating by affecting sweat glands. An antiperspirant may be applied to any part of the body, and are generally applied to the underarms.

A body wash is a liquid product used for cleaning the body during showers. A body wash comprises synthetic detergents derived from either petroleum or plant sources. A body wash has a lower pH value than soap, and is typically less drying to the skin than a soap.

Under one embodiment, a shower gel is synonymous with body wash. Under an alternative embodiment, a shower gel has a higher viscosity than body wash and has a more firm consistency. A shower gel may have an ingredient that has a cooling feel.

A lotion is a low-viscosity topical preparation for application to the skin. Lotions are applied to external skin with bare hands, a brush, or a clean cloth. A lotion, such as a hand lotion or a body lotion, provides smoothing, moisturizing, softening and perfuming of the skin. A lotion may be used as a medicine delivery system.

The personal care product of the present invention comprises a biomimetic blend of short-chain acids. Optionally, the biomimetic blend may further comprise a short chained alcohol or a polyol.

Short-chain acids are acids with less than six carbon atoms. As used herein short-chain acids mean not only hydrocarbyl acids of formula CnH2n+1COOH, wherein n is 0 to 6, but also short-chained acids that are substituted with oxygen containing groups such as alcohols or oxo groups.

Short-chain acids that are hydrocarbyl acids are short-chain fatty acids. Examples of short-chain fatty acids include formic acid, methanoic acid, HCOOH, acetic acid, ethanoic acid, $CH_3COOH$, propionic acid, $CH_3CH_2COOH$, butyric acid, butanoic acid, $CH_3CH_2CH_2COOH$, isobutyric acid, 2-methylpropanoic acid, $(CH_3)_2CHCOOH$, valeric acid, pentanoic acid, $CH_3CH_2CH_2CH_2COOH$, isovaleric acid, 3-methylbutanoic acid, and $(CH_3)_2CHCH_2COOH$.

Examples of short-chain acids comprising one carbon include methanoic acid, formic acid, and HCOOH.

Examples of short-chain acids comprising two carbons include ethanoic acid, acetic acid, $CH_3COOH$, ethanedioic acid, oxalic acid, HOOCCOOH, oxoethanoic acid, glyoxylic acid, formylformic acid, OHCCOOH, 2-hydroxyethanoic acid, glycolic acid, dicarbonous acid, hydroxyacetic acid, and $HOCH_2COOH$.

Examples of short-chain acids comprising three carbons include propanoic acid, ethanecarboxylic acid, $CH_3CH_2COOH$, prop-2-enoic acid, acrylic acid, acroleic acid, ethylenecarboxylic acid, propene acid, vinylformic acid, $CH_2=CH-COOH$, 2-propynoic acid, propiolic acid, acetylene carboxylic acid, propargylic acid, $CH\equiv C-COOH$, propanedioic acid, malonic acid, methanedicarboxylic acid, $HOOC-CH_2-COOH$, 2-hydroxypropanedioic acid, tartronic acid, hydroxymalonic acid, $HOOC-CHOH-COOH$, oxopropanedioic acid, mesoxalic acid, ketomalonic acid, $HOOC-CO-COOH$, 2,2-dihydroxypropanedioic acid, dihydroxymalonic acid, mesoxalic acid monohydrate, $HOOC-C(OH)_2-COOH$, 2-oxopropanoic acid, pyruvic acid, α-ketopropionic acid, acetylformic acid, pyroracemic acid, $CH_3-CO-COOH$, 2-hydroxypropanoic acid, lactic acid, milk acid, $CH_3-CHOH-COOH$, 3-hydroxypropanoic acid, hydracrylic acid, $CH_2OH-CH_2-COOH$, 2,3-dihydroxypropanoic acid, glyceric acid, $CH_2OH-CHOH-COOH$, 2-oxiranecarboxylic acid, and glycidic acid.

Examples of short-chain acids comprising four carbons include butanoic acid, butyric acid, propanecarboxylic acid, $CH_3(CH_2)_2COOH$, 2-methylpropanoic acid, isobutyric acid, isobutanoic acid, $(CH_3)_2CHCOOH$, 2-oxobutanoic acid, alpha-ketobutyric acid, $CH_3-CH_2-CO-COOH$, 3-oxobutanoic acid, acetoacetic acid, $CH_3CO-CH_2-COOH$, 4-oxobutanoic acid, succinic semialdehyde, $HC(O)-CH_2-CH_2-COOH$, (E)-butenedioic acid, fumaric acid, trans-1,2-ethylenedicarboxylic acid, 2-butenedioic acid, trans-butenedioic acid, allomaleic acid, boletic acid, donitic acid, lichenic acid, $HOOC-CH=CH-COOH$, (Z)-butenedioic acid, maleic acid, cis-butenedioic acid, maleinic acid, toxilic acid, $HOOC-CH=CH-COOH$, oxobutanedioic aci, oxaloacetic acid, oxalacetic acid, oxosuccinic acid, $HOOC-CH_2-CO-COOH$, hydroxybutanedioic acid, malic acid, hydroxybutanedioic acid, $HOOC-CH_2-CHOH-COOH$, 2,3-dihydroxybutanedioic acid, tartaric acid, 2,3-dihydroxysuccinic acid, threaric acid, racemic acid, uvic acid, paratartaric acid, $HOOC(CHOH)_2COOH$, (E)-but-2-enoic acid, crotonic acid, trans-2-butenoic acid, beta-methylacrylic acid, 3-methylacrylic acid, (E)-2-butenoic acid, and $CH_3-CH=CH-COOH$.

Examples of short-chain acids comprising five carbons include pentanoic acid, valeric acid, valerianic acid, butane-1-carboxylic acid, $CH_3(CH_2)_3COOH$, 3-methylbutanoic acid, isovaleric acid, $(CH_3)_2CH-CH_2-COOH$, pentanedioic acid, glutaric acid, propane-1,3-dicarboxylic acid, 1,3-propanedicarboxylic acid, n-pyrotartaric acid, $HOOC-(CH_2)_3-COOH$, 2-oxopentanedioic acid, alpha-ketoglutaric acid, 2-ketoglutaric acid, α-ketoglutaric acid, 2-oxoglutaric acid, oxoglutaric acid, and $HOOC-(CH_2)_2-CO-COOH$.

Under one embodiment, the biomimetic blend also comprises a short chain alcohol. Examples of a short chain alcohol includes methanol, $CH_3OH$, ethanol, $CH_3CH_2OH$, n-propanol, 1-propanol, $CH_3-CH_2-CH_2-OH$, iso-propanol, 2-propanol, $(CH_3)_2CH-OH$, n-butanol, 1-bunatol, $CH_3-CH_2-CH_2-CH_2-OH$, sec-butanol, 2-butanol, $CH_3-CH_2-CHOH-CH_3$, iso-butanol, $(CH_3)_2CH-CH_2-OH$, tert-butanol, $(CH_3)_3C-OH$, normal amyl alcohol, pentan-1-ol, $CH_3-(CH_2)_4OH$, isobutyl carbinol, 3-methylbutan-1-ol, isoamyl alcohol, isopentyl alcohol, $(CH_3)_2CH-CH_2-CH_2-OH$, active amyl alcohol, 2-methylbutan-1-ol, $CH_3-CH_2-C(CH_3)H-CH_2-OH$, tertiary butyl carbinol, 2,2-dimethylpropan-1-ol, neopentyl alcohol, $(CH_3)_3C-CH_2-OH$, 3-pentanol, pentan-3-ol, $(CH_3-CH_2)CH-OH$, methylpropyl carbinol, pentan-2-ol, $CH_3-CH_2-CH_2-CH(OH)-CH_3$, methyl isopropyl carbinol, 3-methylbutan-2-ol, $(CH_3)_2CH-C(OH)-CH_3$, dimethyl ethyl carbinol, 2-methylbutan-2-ol, tertiary amyl alcohol, $CH_3-CH_2-C(CH_3)_2-OH$.

Under one embodiment, the biomimetic blend also comprises a short chain polyol. A polyol is an organic compound containing multiple hydroxyl groups. Examples of polyols include a diol, a triol, and a tetrol. An example of a triol is a glycerol.

Lactic acid is a carboxylic acid with the formula $CH_3-CH(OH)-COOH$. Under one embodiment, the lactic acid is L-(+)-lactic acid or (S)-lactic acid. Under another embodiment the lactic acid is D-(−)-lactic acid of (R)-lactic acid. Under yet another embodiment the lactic acid is a mixture of the two stereoisomers.

The personal care composition comprises about 0.1 wt % to about 2.0 wt % of the biomimetic blend. Under one embodiment, the personal care composition comprises about 0.1 wt % to about 0.3 wt % of the biomimetic blend. Under one embodiment, the personal care composition comprises about 0.1 wt % to about 0.5 wt % of the biomimetic blend. Under one embodiment, the personal care composition comprises about 0.1 wt % to about 0.7 wt % of the biomimetic blend. Under one embodiment, the personal care composition comprises about 0.1 wt % to about 1.1 wt % of the biomimetic blend. Under one embodiment, the personal care composition comprises about 0.1 wt % to about 1.3 wt % of the biomimetic blend. Under one embodiment, the personal care composition comprises about 0.1 wt % to about 1.5 wt % of the biomimetic blend. Under one embodiment, the personal care composition comprises about 0.1 wt % to about 1.7 wt % of the biomimetic blend.

Under one embodiment, the personal care composition comprises about 0.3 wt % to about 0.5 wt % of the biomimetic blend. Under one embodiment, the personal care composition comprises about 0.3 wt % to about 0.7 wt % of the biomimetic blend. Under one embodiment, the personal care composition comprises about 0.3 wt % to about 1.1 wt % of the biomimetic blend. Under one embodiment, the personal care composition comprises about 0.3 wt % to about 1.3 wt % of the biomimetic blend. Under one embodiment, the personal care composition comprises about 0.3 wt % to about 1.5 wt % of the biomimetic blend. Under one embodiment, the personal care composition comprises about 0.3 wt % to about 1.7 wt % of the biomimetic blend. Under one embodiment, the personal care composition comprises about 0.3 wt % to about 2.0 wt % of the biomimetic blend.

Under one embodiment, the personal care composition comprises about 0.5 wt % to about 0.7 wt % of the biomimetic blend. Under one embodiment, the personal care composition comprises about 0.5 wt % to about 1.1 wt % of the biomimetic blend. Under one embodiment, the personal care composition comprises about 0.5 wt % to about 1.3 wt % of the biomimetic blend. Under one embodiment, the personal care composition comprises about 0.5 wt % to about 1.5 wt % of the biomimetic blend. Under one embodiment, the personal care composition comprises about 0.5 wt % to about 1.7 wt % of the biomimetic blend. Under one embodiment, the personal care composition comprises about 0.5 wt % to about 2.0 wt % of the biomimetic blend.

Under one embodiment, the personal care composition comprises about 0.7 wt % to about 1.1 wt % of the biomimetic blend. Under one embodiment, the personal care composition comprises about 0.7 wt % to about 1.3 wt % of the biomimetic blend. Under one embodiment, the personal care composition comprises about 0.7 wt % to about 1.5 wt % of the biomimetic blend. Under one embodiment, the personal care composition comprises about 0.7 wt % to about 1.7 wt % of the biomimetic blend. Under one embodiment, the personal care composition comprises about 0.7 wt % to about 2.0 wt % of the biomimetic blend.

Under one embodiment, the personal care composition comprises about 0.9 wt % to about 1.1 wt % of the biomimetic blend. Under one embodiment, the personal care composition comprises about 0.9 wt % to about 1.3 wt % of the biomimetic blend. Under one embodiment, the personal care composition comprises about 0.9 wt % to about 1.5 wt % of the biomimetic blend. Under one embodiment, the personal care composition comprises about 0.9 wt % to about 1.7 wt % of the biomimetic blend. Under one embodiment, the personal care composition comprises about 0.9 wt % to about 2.0 wt % of the biomimetic blend.

Under one embodiment, the personal care composition comprises about 1.1 wt % to about 1.3 wt % of the biomimetic blend. Under one embodiment, the personal care composition comprises about 1.1 wt % to about 1.5 wt % of the biomimetic blend. Under one embodiment, the personal care composition comprises about 1.1 wt % to about 1.7 wt % of the biomimetic blend. Under one embodiment, the personal care composition comprises about 1.1 wt % to about 2.0 wt % of the biomimetic blend.

Under one embodiment, the personal care composition comprises about 1.3 wt % to about 1.5 wt % of the biomimetic blend. Under one embodiment, the personal care composition comprises about 1.3 wt % to about 1.7 wt % of the biomimetic blend. Under one embodiment, the personal care composition comprises about 1.3 wt % to about 2.0 wt % of the biomimetic blend. Under one embodiment, the personal care composition comprises about 1.5 wt % to about 1.7 wt % of the biomimetic blend. Under one embodiment, the personal care composition comprises about 1.5 wt % to about 2.0 wt % of the biomimetic blend. Under one embodiment, the personal care composition comprises about 1.7 wt % to about 2.0 wt % of the biomimetic blend.

Under one embodiment, the personal care product of the present invention comprises a biomimetic blend of short chain acids, wherein the short chain are lactic acid, acetic acid, and pyruvic acid. The lactic is the major component, and the pyruvic acid is the smallest component. Under one embodiment, the biomimetic blend comprises about 8 to about 14 parts by weight lactic acid, about 4 to about 6 parts by weight acetic acid, and about 2 to about 3 parts by weight pyruvic acid. The phrase "parts by weight" refers to the weight ratios of the component short chain acids.

Under one embodiment, the biomimetic blend comprises about 8 to about 10 parts by weight lactic acid, about 4 to about 5 parts by weight acetic acid, and about 2.0 to about 2.5 parts by weight pyruvic acid. Under one embodiment, the biomimetic blend comprises about 8 to about 12 parts by weight lactic acid, about 4 to about 5 parts by weight acetic acid, and about 2.0 to about 2.5 parts by weight pyruvic acid. Under one embodiment, the biomimetic blend comprises about 8 to about 14 parts by weight lactic acid, about 4 to about 5 parts by weight acetic acid, and about 2.0 to about 2.5 parts by weight pyruvic acid. Under one embodiment, the biomimetic blend comprises about 10 to about 12 parts by weight lactic acid, about 4 to about 5 parts by weight acetic acid, and about 2.0 to about 2.5 parts by weight pyruvic acid. Under one embodiment, the biomimetic blend comprises about 10 to about 14 parts by weight lactic acid, about 4 to about 5 parts by weight acetic acid, and about 2.0 to about 2.5 parts by weight pyruvic acid. Under one embodiment, the biomimetic blend comprises about 12 to about 14 parts by weight lactic acid, about 4 to about 5 parts by weight acetic acid, and about 2.0 to about 2.5 parts by weight pyruvic acid.

Under one embodiment, the biomimetic blend comprises about 8 to about 10 parts by weight lactic acid, about 4 to about 6 parts by weight acetic acid, and about 2.0 to about 2.5 parts by weight pyruvic acid. Under one embodiment, the biomimetic blend comprises about 8 to about 12 parts by weight lactic acid, about 4 to about 6 parts by weight acetic acid, and about 2.0 to about 2.5 parts by weight pyruvic acid. Under one embodiment, the biomimetic blend comprises about 8 to about 14 parts by weight lactic acid, about 4 to about 6 parts by weight acetic acid, and about 2.0 to about 2.5 parts by weight pyruvic acid. Under one embodiment, the biomimetic blend comprises about 10 to about 12 parts by weight lactic acid, about 4 to about 6 parts by weight acetic acid, and about 2.0 to about 2.5 parts by weight pyruvic acid. Under one embodiment, the biomimetic blend comprises about 10 to about 14 parts by weight lactic acid, about 4 to about 6 parts by weight acetic acid, and about 2.0 to about 2.5 parts by weight pyruvic acid. Under one embodiment, the biomimetic blend comprises about 12 to about 14 parts by weight lactic acid, about 4 to about 6 parts by weight acetic acid, and about 2.0 to about 2.5 parts by weight pyruvic acid.

Under one embodiment, the biomimetic blend comprises about 8 to about 10 parts by weight lactic acid, about 5 to about 6 parts by weight acetic acid, and about 2.0 to about 2.5 parts by weight pyruvic acid. Under one embodiment, the biomimetic blend comprises about 8 to about 12 parts by weight lactic acid, about 5 to about 6 parts by weight acetic acid, and about 2.0 to about 2.5 parts by weight pyruvic acid. Under one embodiment, the biomimetic blend comprises about 8 to about 14 parts by weight lactic acid, about 5 to about 6 parts by weight acetic acid, and about 2.0 to about 2.5 parts by weight pyruvic acid. Under one embodiment, the biomimetic blend comprises about 10 to about 12 parts by weight lactic acid, about 5 to about 6 parts by weight acetic acid, and about 2.0 to about 2.5 parts by weight pyruvic acid. Under one embodiment, the biomimetic blend comprises about 10 to about 14 parts by weight lactic acid, about 5 to about 6 parts by weight acetic acid, and about 2.0 to about 2.5 parts by weight pyruvic acid. Under one embodiment, the biomimetic blend comprises about 12 to about 14 parts by weight lactic acid, about 5 to about 6 parts by weight acetic acid, and about 2.0 to about 2.5 parts by weight pyruvic acid.

Under one embodiment, the biomimetic blend comprises about 8 to about 10 parts by weight lactic acid, about 4 to about 5 parts by weight acetic acid, and about 2.0 to about 3.0 parts by weight pyruvic acid. Under one embodiment, the biomimetic blend comprises about 8 to about 12 parts by weight lactic acid, about 4 to about 5 parts by weight acetic acid, and about 2.0 to about 3.0 parts by weight pyruvic acid. Under one embodiment, the biomimetic blend comprises about 8 to about 14 parts by weight lactic acid, about 4 to about 5 parts by weight acetic acid, and about 2.0 to about 3.0 parts by weight pyruvic acid. Under one embodiment, the biomimetic blend comprises about 10 to about 12 parts by weight lactic acid, about 4 to about 5 parts by weight acetic acid, and about 2.0 to about 3.0 parts by weight pyruvic acid. Under one embodiment, the biomimetic blend comprises about 10 to about 14 parts by weight lactic acid, about 4 to about 5 parts by weight acetic acid, and about 2.0 to about 3.0 parts by weight pyruvic acid. Under one embodiment, the biomimetic blend comprises about 12 to about 14 parts by weight lactic acid, about 4 to about 5 parts by weight acetic acid, and about 2.0 to about 3.0 parts by weight pyruvic acid.

Under one embodiment, the biomimetic blend comprises about 8 to about 10 parts by weight lactic acid, about 4 to about 6 parts by weight acetic acid, and about 2.0 to about 3.0 parts by weight pyruvic acid. Under one embodiment, the biomimetic blend comprises about 8 to about 12 parts by weight lactic acid, about 4 to about 6 parts by weight acetic acid, and about 2.0 to about 3.0 parts by weight pyruvic acid. Under one embodiment, the biomimetic blend comprises about 8 to about 14 parts by weight lactic acid, about 4 to about 6 parts by weight acetic acid, and about 2.0 to about 3.0 parts by weight pyruvic acid. Under one embodiment, the biomimetic blend comprises about 10 to about 12 parts by weight lactic acid, about 4 to about 6 parts by weight acetic acid, and about 2.0 to about 3.0 parts by weight pyruvic acid. Under one embodiment, the biomimetic blend comprises about 10 to about 14 parts by weight lactic acid, about 4 to about 6 parts by weight acetic acid, and about 2.0 to about 3.0 parts by weight pyruvic acid. Under one embodiment, the biomimetic blend comprises about 12 to about 14 parts by weight lactic acid, about 4 to about 6 parts by weight acetic acid, and about 2.0 to about 3.0 parts by weight pyruvic acid.

Under one embodiment, the biomimetic blend comprises about 8 to about 10 parts by weight lactic acid, about 5 to about 6 parts by weight acetic acid, and about 2.0 to about 3.0 parts by weight pyruvic acid. Under one embodiment, the biomimetic blend comprises about 8 to about 12 parts by weight lactic acid, about 5 to about 6 parts by weight acetic acid, and about 2.0 to about 3.0 parts by weight pyruvic acid. Under one embodiment, the biomimetic blend comprises about 8 to about 14 parts by weight lactic acid, about 5 to about 6 parts by weight acetic acid, and about 2.0 to about 3.0 parts by weight pyruvic acid. Under one embodiment, the biomimetic blend comprises about 10 to about 12 parts by weight lactic acid, about 5 to about 6 parts by weight acetic acid, and about 2.0 to about 3.0 parts by weight pyruvic acid. Under one embodiment, the biomimetic blend comprises about 10 to about 14 parts by weight lactic acid, about 5 to about 6 parts by weight acetic acid, and about 2.0 to about 3.0 parts by weight pyruvic acid. Under one embodiment, the biomimetic blend comprises about 12 to about 14 parts by weight lactic acid, about 5 to about 6 parts by weight acetic acid, and about 2.0 to about 3.0 parts by weight pyruvic acid.

Under one embodiment, the biomimetic blend comprises about 8 to about 10 parts by weight lactic acid, about 4 to about 5 parts by weight acetic acid, and about 2.5 to about 3.0 parts by weight pyruvic acid. Under one embodiment, the biomimetic blend comprises about 8 to about 12 parts by weight lactic acid, about 4 to about 5 parts by weight acetic acid, and about 2.5 to about 3.0 parts by weight pyruvic acid. Under one embodiment, the biomimetic blend comprises about 8 to about 14 parts by weight lactic acid, about 4 to about 5 parts by weight acetic acid, and about 2.5 to about 3.0 parts by weight pyruvic acid. Under one embodiment, the biomimetic blend comprises about 10 to about 12 parts by weight lactic acid, about 4 to about 5 parts by weight acetic acid, and about 2.5 to about 3.0 parts by weight pyruvic acid. Under one embodiment, the biomimetic blend comprises about 10 to about 14 parts by weight lactic acid, about 4 to about 5 parts by weight acetic acid, and about 2.5 to about 3.0 parts by weight pyruvic acid. Under one embodiment, the biomimetic blend comprises about 12 to about 14 parts by weight lactic acid, about 4 to about 5 parts by weight acetic acid, and about 2.5 to about 3.0 parts by weight pyruvic acid.

Under one embodiment, the biomimetic blend comprises about 8 to about 10 parts by weight lactic acid, about 4 to about 6 parts by weight acetic acid, and about 2.5 to about 3.0 parts by weight pyruvic acid. Under one embodiment, the biomimetic blend comprises about 8 to about 12 parts by weight lactic acid, about 4 to about 6 parts by weight acetic acid, and about 2.5 to about 3.0 parts by weight pyruvic acid. Under one embodiment, the biomimetic blend comprises about 8 to about 14 parts by weight lactic acid, about 4 to about 6 parts by weight acetic acid, and about 2.5 to about 3.0 parts by weight pyruvic acid. Under one embodiment, the biomimetic blend comprises about 10 to about 12 parts by weight lactic acid, about 4 to about 6 parts by weight acetic acid, and about 2.5 to about 3.0 parts by weight pyruvic acid. Under one embodiment, the biomimetic blend comprises about 10 to about 14 parts by weight lactic acid, about 4 to about 6 parts by weight acetic acid, and about 2.5 to about 3.0 parts by weight pyruvic acid. Under one embodiment, the biomimetic blend comprises about 12 to about 14 parts by weight lactic acid, about 4 to about 6 parts by weight acetic acid, and about 2.5 to about 3.0 parts by weight pyruvic acid.

Under one embodiment, the biomimetic blend comprises about 8 to about 10 parts by weight lactic acid, about 5 to about 6 parts by weight acetic acid, and about 2.5 to about 3.0 parts by weight pyruvic acid. Under one embodiment, the biomimetic blend comprises about 8 to about 12 parts by weight lactic acid, about 5 to about 6 parts by weight acetic acid, and about 2.5 to about 3.0 parts by weight pyruvic acid. Under one embodiment, the biomimetic blend comprises about 8 to about 14 parts by weight lactic acid, about 5 to about 6 parts by weight acetic acid, and about 2.5 to about 3.0 parts by weight pyruvic acid. Under one embodiment, the biomimetic blend comprises about 10 to about 12 parts by weight lactic acid, about 5 to about 6 parts by weight acetic acid, and about 2.5 to about 3.0 parts by weight pyruvic acid. Under one embodiment, the biomimetic blend comprises about 10 to about 14 parts by weight lactic acid, about 5 to about 6 parts by weight acetic acid, and about 2.5 to about 3.0 parts by weight pyruvic acid. Under one embodiment, the biomimetic blend comprises about 12 to about 14 parts by weight lactic acid, about 5 to about 6 parts by weight acetic acid, and about 2.5 to about 3.0 parts by weight pyruvic acid.

Under one embodiment, the biomimetic blend comprises about 8 to about 14 parts by weight lactic acid, about 4 to about 6 parts by weight acetic acid, and about 2.0 to about 3.0 parts by weight pyruvic acid, and about 1 part of glycerol.

In some embodiments, the personal care composition includes a surfactant. The surfactant can be any anionic, nonionic, amphoteric, or zwitterionic surfactant, or combinations thereof. The amount of surfactant in the composition is at least 1 weight %. In other embodiments, the amount is 1 to 20 weight %, or at least 2, 3, 4, 5, 6, 7, 8, 9, or 10 weight %.

Under various embodiments, surfactants make up 10, 20, 30, 40, or 50 percent of the personal care composition. Under an embodiment, multiple surfactants are used to achieve desired product qualities. A primary surfactant provides good foaming ability and cleaning effectiveness, while a secondary surfactant adds qualities of mildness to prevent irritation or over-drying of the skin. To prevent ingredients from separating, emulsifiers such as diethanolamine may be added. Additional ingredients include conditioning agents that moisturize the skin during and after product use. Ingredients, like scent in the form of essential oils or fragrance oils, and colorant in the form of water soluble dyes may also be used.

A variety of anionic surfactants can be utilized in the personal care composition including, for example, long chain alkyl ($C_6$-$C_{22}$) materials such as long chain alkyl sulfates, long chain alkyl sulfonates, long chain alkyl phosphates, long chain alkyl ether sulfates, long chain alkyl alpha olefin sulfonates, long chain alkyl taurates, long chain alkyl isethionates (SCI), long chain alkyl glyceryl ether sulfonates (AGES), sulfosuccinates and the like. These anionic surfactants can be alkoxylated, for example, ethoxylated, although alkoxylation is not required. These surfactants are typically highly water soluble as their sodium, potassium, alkyl and ammonium or alkanol ammonium containing salt form and can provide high foaming cleansing power. Other equivalent anionic surfactants may be used. In one embodiment, the anionic surfactant comprises sodium laureth sulfate, sodium pareth sulfate, and combinations thereof. Anionic surfactants can be included in any desired amount. In one embodiment, anionic surfactants are present in the composition in an amount of 0 to about 15% by weight. In one embodiment, anionic surfactants are present in an amount of about 6 to about 8% by weight.

Amphoteric surfactants may also be included in the composition. These surfactants are typically characterized by a combination of high surfactant activity, lather forming and mildness. Amphoteric surfactants include, but are not limited to derivatives of aliphatic secondary and tertiary amines in which the aliphatic radical can be straight chain or branched and wherein one of the aliphatic substituents contains about 8 to about 18 carbon atoms and one contains an anionic water solubilizing group, e.g., carboxy, sulfonate, sulfate, phosphate, or phosphonate. Examples of such compounds include sodium 3-dodecyaminopropionate, sodium 3-dodecylaminopropane sulfonate, N-alkyl taurines and N-higher alkyl aspartic acids. Other equivalent amphoteric surfactants may be used. Examples of amphoteric surfactants include, but are not limited to, a range of betaines including, for example, high alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxyethyl)carboxymethyl betaine, oleyl dimethyl gamma-carboxypropyl betaine, and lauryl bis-(2-hydroxypropyl)alpha-carboxyethyl betaine, sulfobetaines such as coco dimethyl sulfopropyl betaine, stearyl dimethyl sulfopropyl betaine, amido betaines, amidosulfobetaines and the like. Betaines having a long chain alkyl group, particularly coco, may be particularly useful as are those that include an amido groups such as the cocamidopropyl and cocoamidoethyl betaines. Amphoteric surfactants can be included in any desired amount. In one embodiment, amphoteric surfactants are present in the composition in an amount of 0 to about 15% by weight. In one embodiment, the amphoteric surfactants are present in the composition in an amount of about 4 to about 6% by weight.

Examples of nonionic surfactants include polysorbate 20, long chain alkyl glucosides having $C_8$-$C_{22}$ alkyl groups; coconut fatty acid monoethanolamides such as cocamide MEA; coconut fatty acid diethanolamides, fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols); polypropylene glycol ethoxylates (for example the PLURONIC™ block copolymers commercially available from BASF); fatty acid alkylolamides, (fatty acid amide polyethylene glycols); N-alkyl-, N-alkoxypolyhydroxy fatty acid amides; sucrose esters; sorbitol esters; polyglycol ethers; and combinations thereof. Nonionic surfactants can be included in any desired amount. In one embodiment, nonionic surfactants are present in the composition in an amount of 0 to about 3% by weight. In one embodiment, nonionic surfactants are present in the composition in an amount of about 0.5 to about 1.5% by weight.

Cationic surfactants can also be included in the composition. Examples of cationic surfactants include any quaternium or polyquaternium compound. Cationic surfactants can be included at any desired level. In one embodiment, cationic surfactants are present in the composition in an amount of 0 to about 2% by weight. In one embodiment, cationic surfactants are present in the composition in an amount of about 0.1 to about 0.3% by weight.

Additional ingredients may be present in the personal care composition. These include water and ingredients to thicken, preserve, emulsify, add fragrance, and color.

Skin compatible oils can be included in the composition. Skin compatible oils include a range of liquid hydrocarbons, for example, linear and branched oils such as liquid paraffin, squalene, squalane, mineral oil, low viscosity synthetic hydrocarbons such as polyalphaolefins, commercially available from ExxonMobil under the trade name PURESYN PAO and polybutene under the trade name PANALANE™ or INDOPOL™. Light (low viscosity) highly branched hydrocarbon oils may also be suitable in some instances. Other useful skin compatible oils may be silicone based, for example, linear and cyclic polydimethyl siloxane, organo functional silicones (alkyl and alkyl aryl), and amino silicones.

In other embodiments, the composition may include any of following materials in any desired amount to achieve a desired effect in the composition (amounts that can be used in some embodiments are provided): one or more alkaline salts, for example, sodium chloride, sodium sulfate, sodium carbonate, sodium bicarbonate and/or their equivalents (0 to 5% by weight); foaming agents, for example decyl glucoside, and/or their equivalents (0 to 3% by weight); glyceryl esters and derivatives, for example glycol distearate, and/or their equivalents (0 to 3%; by weight); sequestrants, for example, tetrasodium EDTA, and/or their equivalents (0 to 2% by weight); biocides, for example, Triclosan (2,4,4'-trichloro-2'-hydroxydiphenyl ether), DMDM hydantoin, formaldehyde and/or imidazolidinyl urea, and/or their equivalents (0 to 2% by weight); organic acids, for example, citric acid and/or formic acid and/or their equivalents (0 to 2% by weight); viscosity modifiers (0 to 2% by weight); fragrances and/or perfumes (0 to 5% by weight); preservatives, for example, phenoxyethanol, formaldehyde solution, parabens, pentanediol or sorbic acid (0 to 2% by weight); pearlizing agents, for example, glycol distearic esters, such as ethylene glycol distearate, but also fatty acid monoglycol esters (0 to 3% by weight); stabilizers, for example, metal salts of fatty acids, such as e.g. magnesium stearate, aluminum stearate and/or zinc stearate (0 to 2% by a weight); and dyes and pigments that are approved and suitable for cosmetic purposes.

Water may be included in the composition. Water can be included in an amount of 0 to about 90% by weight. In one embodiment, water is present at about 50% to about 90% by weight.

In one embodiment, a moisturizing body wash composition also utilizes, as a thickening agent, a blend of PEG-150 distearate and PPG-2 hydroxyethyl cocamide for countering a decrease in viscosity associated with the concentrations of moisturizing agents utilized in some embodiments of the moisturizing body wash composition. This blended thickening agent allows the composition to achieve viscosities beyond those that could be achieved with conventional thickening agents, for example sodium chloride alone, and is able to achieve suitable viscosities at relatively low concentrations. The relatively low concentrations used to achieve the desired viscosities are also advantageous with respect to manufacturing processes that may be employed to manufacture the moisturizing body wash composition, thereby reducing the need for larger equipment or modifications and the capital expenditure associated with manufacturing the moisturizing body wash composition if other thickening agents were used. The PEG-150 distearate and the PPG-2 hydroxyethyl cocamide can be present in any amount to achieve a desired viscosity. In one embodiment, the amount of PEG-150 distearate in the composition is 0 to about 2% by weight. In one embodiment, the amount of PPG-2 hydroxyethyl cocamide in the composition is 0 to about 2% by weight. In one embodiment, the weight ratio of the PEG-150 distearate to the PPG-2 hydroxyethyl cocamide can be about 3:1 to about 1:3. In one embodiment the PEG-150 distearate and the PPG-2 hydroxyethyl cocamide are each present at 0.0225% by weight. The PEG-150 distearate and the PPG-2 hydroxyethyl cocamide are available as a mixture from Uniqema under the trade name PROMIDIUM™ LTS.

Microbeads may also be added to the personal care composition. Microbeads are microspheres that may added to a variety of cosmetic products for their exfoliating qualities.

Personal care composition may also contain the ingredient menthol, which gives a cooling and stimulating sensation on the skin, and some men's shower gels are also designed specifically for use on hair and body. Shower gels contain milder surfactant bases than shampoos, and some also contain gentle conditioning agents in the formula. This means that shower gels can also double as an effective and perfectly acceptable substitute to shampoo, even if they are not labelled as a hair and body wash. Washing hair with shower gel should give approximately the same result as using a moisturizing shampoo The present invention is also directed to a method of treating a skin of a patient in need thereof, the method comprising administering to the skin the above described composition, effective to promote the growth of beneficial bacteria and inhibit the growth of harmful bacteria, wherein the beneficial bacterium is selected from the group consisting of *S. epidermidis*, and harmful bacteria is selected from the group consisting of *E. coli, C. straitum*, and *S. aureus*.

The composition is spread on the skin neat, or it may be admixed with water. The spreading of the personal care composition may be done by hand, or it may be done by a instrument such as a glove or a piece of cloth.

The method of applying the personal care composition leaves behind a film. The thickness of the film depends on other parts of the formulation, but for a lotion, the thickness will be comparable to the thicknesses of other lotions, body washes, or deodorants. For those embodiments wherein the personal care composition is a lotion, the thickness is about 50 μm.

The present invention is also directed to the method of treating a skin of a patient, wherein the amount of harmful bacteria is lowered by at least about 10%, as measured after 48 hours on a 50 μm thick layer of personal care composition comprising 0.6 wt % biomimetic blend, compared to the personal care composition not comprising the biomimetic blend.

The present invention is also directed to the method of treating a skin of a patient, wherein the amount of beneficial bacteria is raised by at least about 10%, as measured after 48 hours on a 50 μm thick layer of personal care composition comprising 0.6 wt % biomimetic blend, compared to the personal care composition not comprising the biomimetic blend.

For avoidance of doubt, salts and derivatives of any one of the short chain fatty acids described herein, would be suitable for use in the personal care compositions of the present invention.

EXAMPLES

Example 1

A probiotic complex was prepared by the byproduct of *Lactobacillus rhamnosus* fermented with xylitol. A pure colony of each *lactobacillus* species was grown in MRS agar in 5% $CO_2$ incubator at 37° C. overnight. The turbidity of the *lactobacillus* solution was adjusted to optical density of 0.1 at 610 nm using a UV-VIS Spectrometer. About 4.0 mL of *lactobacillus* culture with optical density of 0.1 was added to 20 mL of MRS medium with 2.5% xylitol, and incubated in 5% $CO_2$ at 37° C. overnight. Next day, the turbidity of the *lactobacillus* culture was adjusted to optical density of 1 using sterile distilled water, then centrifuged 12,000 rpm for 10 min. The supernatant was collected and then passed through a 0.22 μm filter. The *lactobacillus* ferment was analyzed via HPLC and was found to comprise the composition presented in Table 1.

TABLE 1

| SCFA | Sample 1 (mg/g) |
|---|---|
| Glycerol | 0.32 |

TABLE 1-continued

| SCFA | Sample 1 (mg/g) |
|---|---|
| Pyruvic acid | 0.84 |
| Lactic acid | 3.63 |
| Acetic acid | 1.61 |

The weight ratio of the three short chain fatty acids, lactic acid, acetic acid and pyruvic acid were found to be in an approximate ratio of 4:2:1.

Example 2

A growth inhibition assay was conducted to evaluate the anti-microbial efficacy of an exemplary complex of the present invention comprising a plurality of short chain fatty acids (e.g., lactic acid, acetic acid and pyruvic acid) in an approximate weight ratio of 4:2:1, respectively. The bacteria selected were those that often found on human skin. In particular, a pure colony of *Escherichia coli, Corynebacterium striatum, Staphylococcus aureus*, and *Staphylococcus epidermidis* were grown in TSB medium overnight. The turbidity of the bacterial culture solution was adjusted to optical density of 0.1 at 610 nm using a UV-VIS Spectrometer. Then, 2 mL of the bacteria culture solution was incubated with 2 mL of 0.6% of a composition comprising an exemplary complex of the present invention at 37° C. for forty-eight (48) hours. The bacteria incubated with medium alone was considered the control.

The turbidity of each tube was read after incubation. Replicates were run for each treatment. The average optical density of the blend was adjusted by subtracting the optical density of the control. The results are described in Table 2 (below). Negative values indicate that the blend inhibits bacteria growth, and positive values indicate that the blend promotes the growth of bacteria.

TABLE 2

| Bacterium | Adjusted Optical Density |
|---|---|
| E. coli | (−) 1.71 |
| C. striatum | (−) 0.86 |
| S. aureus | (−) 0.49 |
| Control | 0 |
| S. epidermidis | (+) 0.16 |

The above data shows that after a 48-hour incubation period, an exemplary complex of the present invention inhibits the growth of *E. coli, C. striatum* and *S. aureus*, while promoting *S. epidermidis*.

Example 3

EpiDerm™ skin tissue (obtained from MatTek Corporation, Ashland, Mass., USA), was used to test in vitro skin benefit of the exemplary complex of the present invention in a body wash backbone. Body washes were formulated with or without an exemplary complex of the present invention (diluted to 1% solution). Fifty (50) μL of each body wash was applied on a tissue sample for 15 min, then washed with PBS several times, then the tissues were incubated for 5 days. After 5 days, the tissues were collected, RNA was extracted. Gene expression analysis was done by qPCR. The result showed the body wash containing an exemplary complex of the present invention upregulated AQP (hydration), FASN (barrier), OCLN (tight junction) gene expression and downregulated IL8 (inflammation) expression when compared to the body wash without the exemplary complex of the present invention.

NativeSkin® models (Genoskin, Toulouse, France), were used to test the ex vivo skin benefit of the exemplary complex of the present invention in a body lotion backbone. Skin biopsies collected from human donor were tape striped using 50 consecutive take strips (MonaDerm, DS100) prior to models production to remove stratum cornerum. The skin tissues were cultured under cell culture conditions (37° C., 5% CO2 and max humidity) for either 3 or 5 days with 1 mL standard Nativeskin® medium. 5 μL formulation was topically applied onto the skin surface. After 3 day and 5 days incubation, the skins were collected for terminal differentiation biomarkers analysis. The results showed that the body lotion containing an exemplary complex of the present invention improved skin barrier function and hydration by increasing the expression of Filaggrin and Occludin when compared to the body wash without the exemplary complex of the present invention.

Example 4

A growth inhibition assay was conducted to evaluate the effect that another exemplary combination of short chain fatty acids—lactic acid, acetic acid and succinic acid (Sample 2)—has on the inhibition or growth of bacteria commonly found on the skin. Pure colonies of *E. coli, C. striatum, S. aureus* and *S. epidermidis* were grown in TSB medium overnight. The turbidity of the bacterial culture solution was adjusted to OD=0.1 (Optical Density) at 610 nm using a UV-VIS Spectrometer. Two (2) ml of the bacteria culture solution was incubated with two (2) ml of 0.6% Sample 2 and the Control at 37° C. for forty-eight (48) hours. The bacteria incubated with medium alone was considered the Control. The turbidity of each tube was read after incubation. Replicates were run for each treatment. If the value is negative, the sample inhibits bacteria growth, if the value is positive, the sample promotes the growth of bacteria. As described in FIG. 1, 0.6% of an exemplary composition of the present invention inhibited the growth of *E. coli, C. striatum* and *S. aureus*, but promoted *S. epidermidis*. This selective effect is truly unexpected in view of the recognized benefits provided by the short chain fatty acids individually.

Example 5

A constant ratio dose-dependent study of 50% tyrosinase inhibition was conducted to investigate the dose reduction enabled by exemplary compositions of the present invention. As described by the data reported in Table 3 (below) a strong synergy between lactic acid, acetic acid and pyruvic acid was confirmed.

TABLE 3

| Sample | Dose (Wt. %) | | |
|---|---|---|---|
| Lactic Acid (L) | 0.42543 | — | |
| Acetic Acid (A) | — | 0.61047 | |
| Pyruvic Acid (P) | | | 0.09641 |
| L + A + P | 0.02928 | 0.01464 | 0.00732 |

Example 6

A constant ratio dose-dependent study of collagenase and elastase inhibition was conducted to investigate the dose reduction enabled by exemplary compositions of the present invention. As described by the data reported in Table 4 (below) a strong synergy between lactic acid, acetic acid and pyruvic acid was confirmed.

TABLE 4

| Sample | Dose | | |
|---|---|---|---|
| Lactic Acid (L) | 1.19545 | — | |
| Acetic Acid (A) | — | 5.45279 | |
| Pyruvic Acid (P) | | | 0.51504 |
| L + A + P | 0.64674 | 0.32337 | 0.16169 |

Example 7

Figure 2:
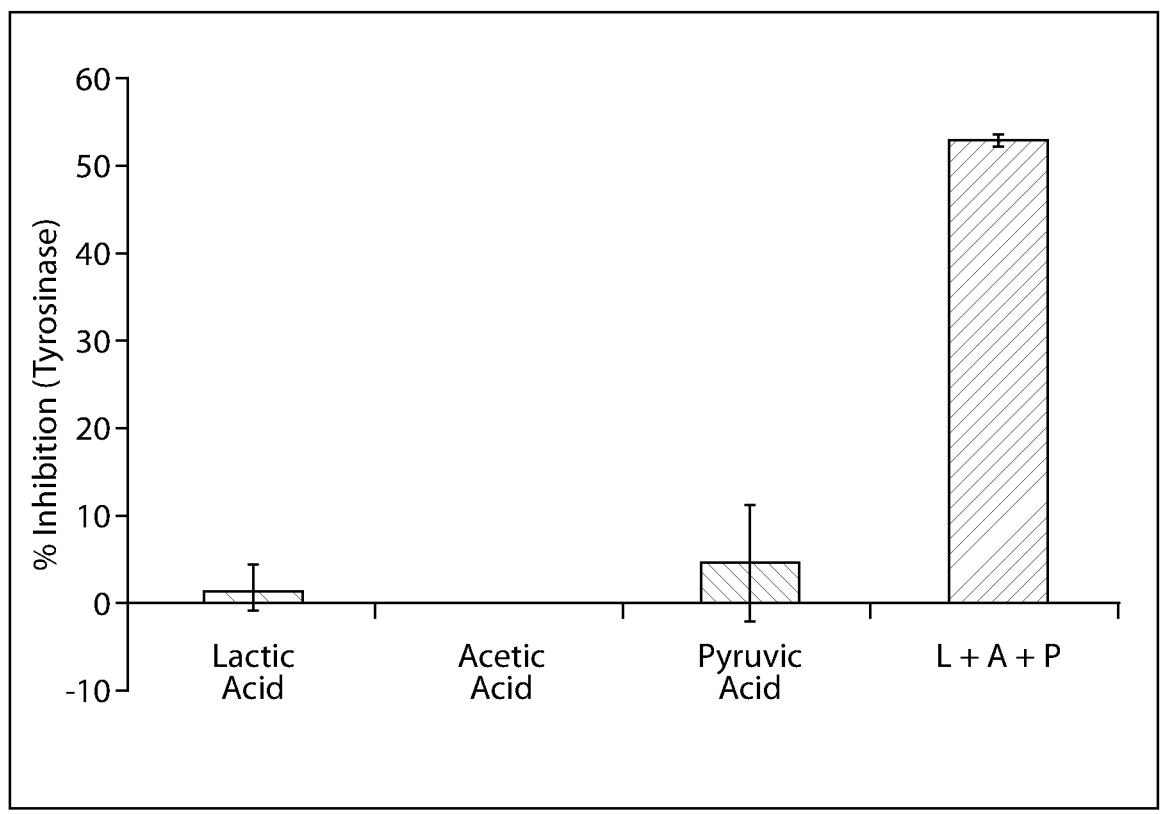
FIG. 2 depicts a comparison of the tyrosinase inhibition provided by an exemplary composition of the present invention and individual short chain fatty acids.

A study of tyrosinase inhibition is conducted (e.g., Sigma Aldrich MAK 257 Kit) to investigate the efficacy of an exemplary composition of the present invention (0.156 wt. % lactic acid; 0.078 wt. % acetic acid; and 0.039 wt. % pyruvic acid) and individual short chain fatty acids at the same concentrations. As described by the data reported in FIG. 2 a strong synergy between lactic acid, acetic acid and pyruvic acid was confirmed.

Example 8

Figure 3:
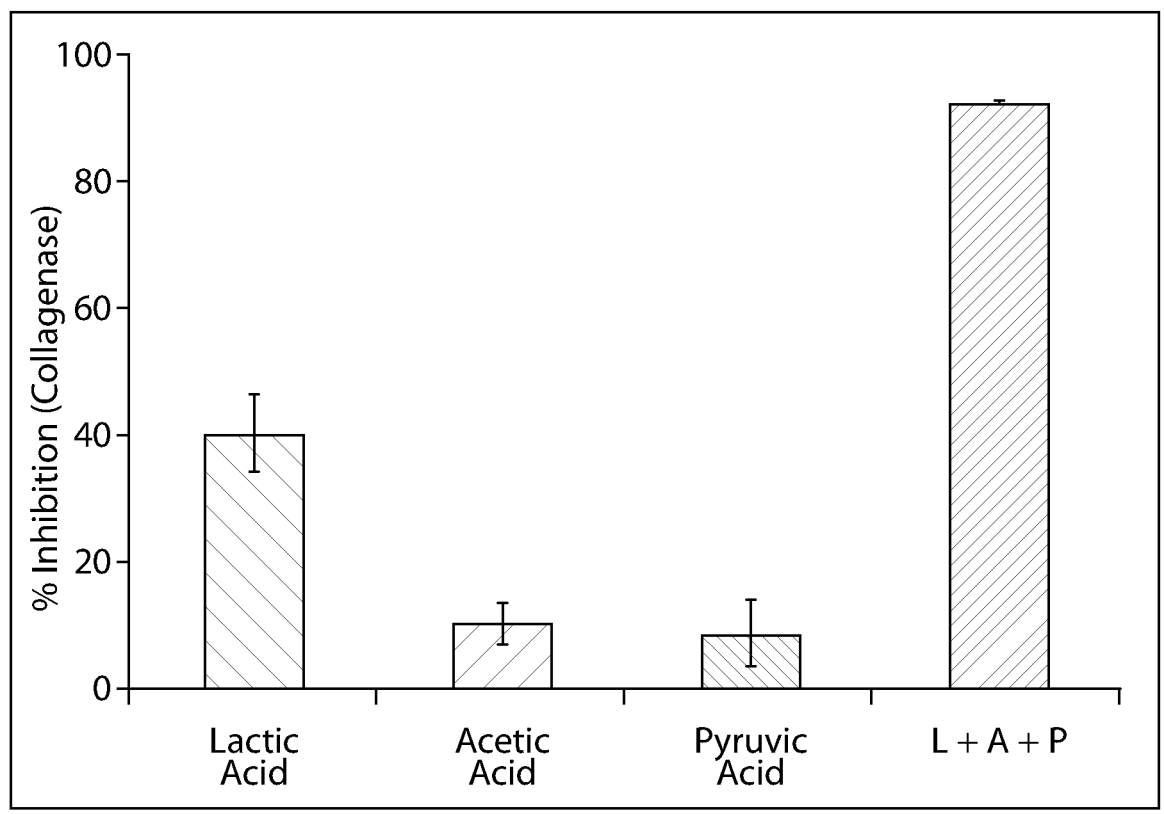
FIG. 3 depicts a comparison of the collagenase inhibition provided by an exemplary composition of the present invention and individual short chain fatty acids.

A study of collagenase inhibition is conducted (e.g., Sigma Aldrich MAK 293 Kit) to investigate the efficacy of an exemplary composition of the present invention (1.25 wt. % lactic acid; 0.625 wt. % acetic acid; and 0.312 wt. % pyruvic acid) and individual short chain fatty acids at the same concentrations. As described by the data reported in FIG. 3 a strong synergy between lactic acid, acetic acid and pyruvic acid was confirmed.

Example 9

Figure 4:
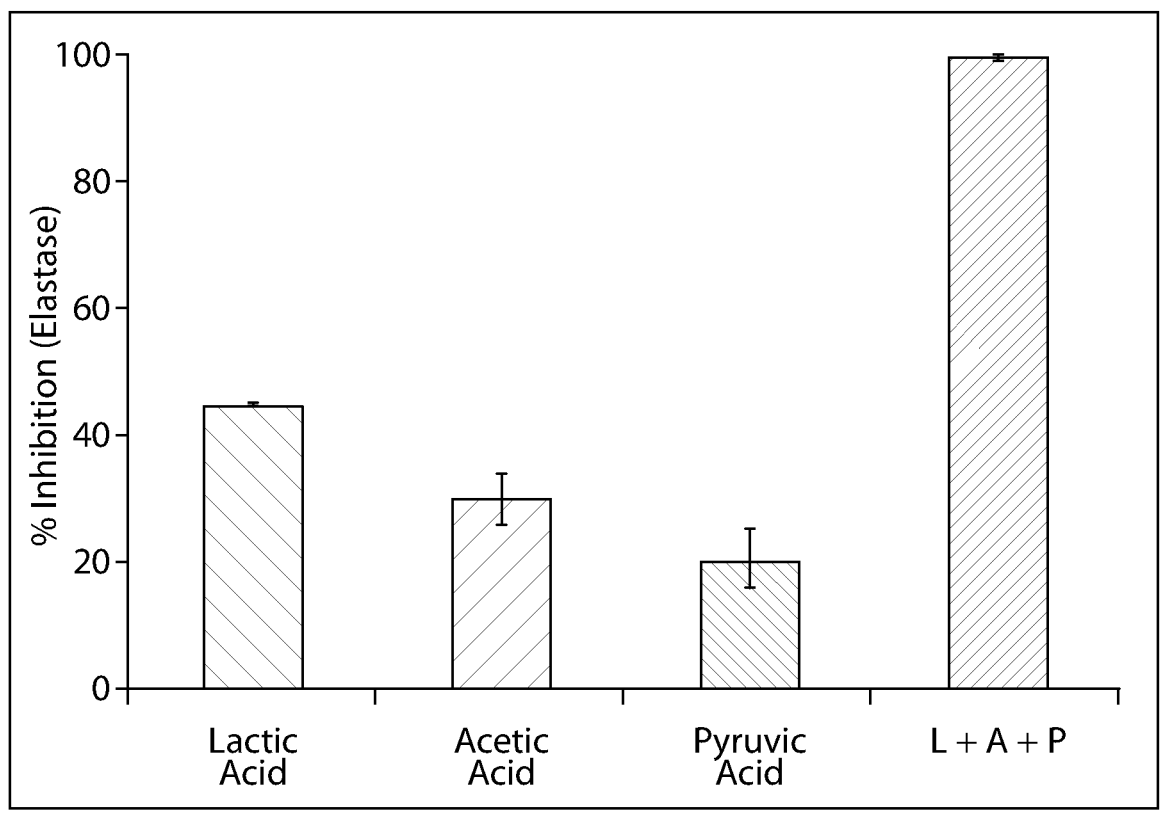
FIG. 4 depicts a comparison of the elastase inhibition provided by an exemplary composition of the present invention and individual short chain fatty acids.

A study of elastase inhibition is conducted (e.g., Sigma Aldrich MAK 213 Kit) to investigate the efficacy of an exemplary composition of the present invention (0.625 wt. % lactic acid; 0.312 wt. % acetic acid; and 0.156 wt. % pyruvic acid) and individual short chain fatty acids. As described by the data reported in FIG. 4 a strong synergy between lactic acid, acetic acid and pyruvic acid was confirmed.

The present invention has been described with reference to several embodiments. Such embodiments are merely exemplary and are not intended to be limiting. Further, it will be apparent to those skilled in the art that numerous changes may be made in such details without departing from the spirit and the principles of the invention recited in the claims appended hereto.

What is claimed is:

1. A personal care composition comprising:
   a cosmetically acceptable carrier; and
   a biomimetic blend consisting of:
      from about 2 to about 16 parts, by weight, lactic acid or a salt thereof;
      from about 1 to about 8 parts, by weight, acetic acid or a salt thereof;
      from about 0.5 to about 4 parts, by weight, pyruvic acid or a salt thereof; and
      1 part, by weight, glycerol wherein a ratio of lactic acid: acetic acid: pyruvic acid is 4:2:1;
   wherein the personal care composition treats a symptom associated with a disease, disorder or condition of skin caused by the presence of harmful bacteria or a lack of beneficial bacteria.

2. The personal care composition according to claim 1, wherein the cosmetically acceptable carrier comprises an ingredient selected from the group consisting of a fragrance; a surfactant; a thickening agent; and a combination of two or more thereof.

3. The personal care composition according to claim 1, wherein the composition is in a form selected from the group consisting of a body wash; a hand soap; a shower gel; a wipe; a lotion; a cream; an ointment; an antiperspirant; and a deodorant.

4. The personal care composition according to claim 3, wherein the antiperspirant and deodorant are in a form selected from the group consisting of an aerosol; a roll-on; and a stick.

5. A method of treating a symptom associated with a disease, disorder or condition of skin caused by the presence of harmful bacteria or a lack of beneficial bacteria, comprising administering to the skin of a subject in need thereof, an effective amount of a personal care composition comprising:
   a cosmetically acceptable carrier; and
   a biomimetic blend consisting of:
      from about 2 to about 16 parts, by weight, lactic acid or a salt thereof;
      from about 1 to about 8 parts, by weight, acetic acid or a salt thereof;
      from about 0.5 to about 4 parts, by weight, pyruvic acid or a salt thereof;
      1 part, by weight, glycerol wherein a ratio of the lactic acid: acetic acid: pyruvic acid is 4:2:1; and
   wherein the harmful bacteria comprises: *Escherichia coli, Corynebacterium striatum*, or *Staphylococcus aureus*;
   wherein the beneficial bacteria comprises *Staphylococcus epidermidis*;
   wherein the disease, disorder, or condition of skin is selected from the group consisting of small benign boils; folliculitis; impetigo; cellulitis; atopic dermatitis, more commonly known as eczema; and staphylococcal scalded skin syndrome; and
   wherein the personal care composition is administered in an amount effective to promote growth of beneficial bacteria and/or inhibit growth of harmful bacteria.

6. A method for inhibiting:
   tyrosinase;
   collagenase; and
   elastase;
   in a patient in need thereof, comprising administering to skin of said patient, an effective amount of the personal care composition according to claim 1.

7. The personal care composition of claim 1, wherein the salt of pyruvic acid is sodium pyruvate.

* * * * *